United States Patent [19]

Pregaglia et al.

[11] Patent Number: 4,783,561

[45] Date of Patent: Nov. 8, 1988

[54] PROCESS FOR THE PREPARATION OF HALOGENATED (2,2)-PARACYCLOPHANES AND MIXTURES OF RESULTANT HALOGENATED (2,2)-PARACYCLOPHANES

[75] Inventors: Gian Franco Pregaglia; Maurizio A. Beretta; Alessandro Malacrida, all of Milan, Italy

[73] Assignee: Montedison S.p.A., Milan, Italy

[21] Appl. No.: 924,275

[22] Filed: Oct. 29, 1986

[30] Foreign Application Priority Data

Oct. 30, 1985 [IT] Italy .............................. 22668 A/85

[51] Int. Cl.$^4$ ...................... C07C 21/24; C07C 25/18
[52] U.S. Cl. .................................... 570/183; 570/184
[58] Field of Search ............... 570/183, 184, 143, 141, 570/142, 190, 201, 129; 564/282

[56] References Cited

U.S. PATENT DOCUMENTS

| | | | |
|---|---|---|---|
| 3,221,068 | 11/1965 | Gorham | 570/184 |
| 3,349,142 | 10/1967 | Yeh | 570/183 |
| 4,532,369 | 7/1985 | Hartner | 585/428 |

FOREIGN PATENT DOCUMENTS

| | | | |
|---|---|---|---|
| 704487 | 2/1965 | Canada | 570/129 |
| 807196 | 1/1959 | United Kingdom | 564/282 |

OTHER PUBLICATIONS

Reich et al., JACS 91:13, pp. 3527–3532, 3534–3543.

*Primary Examiner*—Werren B. Lone
*Attorney, Agent, or Firm*—Stevens, Davis, Miller & Mosher

[57] ABSTRACT

There is disclosed a process for the preparation of halogenated (2,2)-paracyclophanes by Hofmann elimination, in an alkaline medium, from p.methylbenzyltrimethylammonium hydroxide halogen-substituted in the nucleus.

11 Claims, No Drawings

PROCESS FOR THE PREPARATION OF HALOGENATED (2,2)-PARACYCLOPHANES AND MIXTURES OF RESULTANT HALOGENATED (2,2)-PARACYCLOPHANES

The present invention relates to a process for the preparation of halogenated derivatives of (2,2)-paracyclophane and to mixtures of the resultant halogenated (2,2)-paracyclophanes having the desired degree of substitution and a high degree of purity.

BACKGROUND OF THE INVENTION

The halogenated derivatives of (2,2)-paracyclophane having general formula:

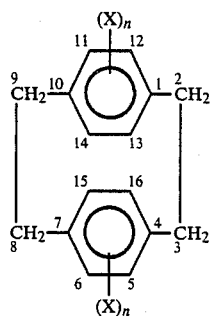

in which X is a halogen and in particular chlorine, and n is an integer from 1 to 4, and in particular dichloro-(2,2)-paracyclophane and tetrachloro-(2,2)-paracyclophane, are well known in literature and are generally utilized as intermediates in the preparation of the corresponding chlorinated poly-p.xylylene.

Said halogenated derivatives of (2,2)-paracyclophane, and in particular the chlorinated derivatives of said compound, are usefully employed in the preparation of films in the field of the conforming coating by application according to the technique based on vacuum vapor deposition and polymerization in situ.

For this kind of application, as is well known, the halogenated starting products must have certain characteristics, namely:

(a) they must be pure, i.e., they must consist of compounds having the desired degree of substitution, in order to obtain a satisfactory homogeneity of the films, and (b) the isomeric composition of the fractions, at the same degree of substitution, must be constant, in order to have the same conditions of application and the same chemical-physical characteristics of the films obtained.

The method generally followed for the preparation of the halogenated derivatives of (2,2)-paracyclophane is that of subjecting to halogenation the previously formed (2,2)-paracyclophane, which is obtained by carrying out the Hofmann elimination from p.methylbenzyltrimethylammonium hydroxide, of formula:

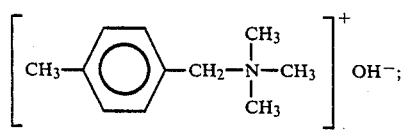

by this halogenation process carried out on previously formed (2,2)-paracyclophane it is not possible to prevent the generation of appreciable amounts of undesirable products. In particular, in the case of a dichlorination process, there are obtained not only the desired dichlorinated isomers of (2,2)-paracyclophane containing one chlorine atom on each ring, but also the undesired isomers having two chlorine atoms on one ring only and those with only one chlorine atom and/or with three chlorine atoms. These by-products lead, during the polymerization step, to the formation of copolymers of p-xylylene, chloro-p-xylylene and dichloro-p-xylylene having a high nonhomogeneity in the distribution of chlorine on the rings of the polymeric chains. Furthermore, from these isomer mixtures it is impossible, by means of the conventional separation techniques, to obtain only the di-halogenated isomers having an equal number of halogen atoms on each ring.

THE PRESENT INVENTION

We have now found that halogenated isomers of (2,2)-paracyclophane, having the same total halogen content and the same number of halogen atoms in the individual rings, are obtainable by Hofmann elimination, in an alkaline aqueous solution, from p.methylbenzyltrimethylammonium hydroxide halogen-substituted in the nucleus, of formula:

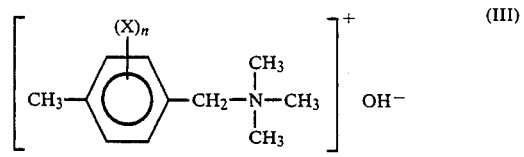

in which X is a halogen atom, in particular chlorine, and n is an integer from 1 to 4, in which the concentration of alkaline hydroxide in the aqueous solution is maintained lower than 40% by weight and preferably constant during the elimination reaction.

It is specifically pointed out that the alkaline solution concentration is an indispensable parameter for obtaining, with industrially acceptable yields, i.e., higher than 25% by moles, the halogenated isomers of (2,2)-paracyclophane having the same number of halogen atoms in the individual rings and the same total halogen content. In fact, if Hofmann elimination is conducted in an alkaline medium at a higher concentration, polyhalogen-p.xylylenes are essentially formed, as is described in British patent No. 807,196.

The halogen-substituted p.methylbenzyltrimethylammonium hydroxide of formula (III) can be prepared starting from the corresponding halide according to any known process. For example, it can be formed in situ by reacting an alkaline hydroxide with the corresponding halide, or it can be pre-formed by eluting an aqueous solution of the halide through a basic ion-exchange resin column, or by treatment with silver oxide.

The p.methylbenzyltrimethylammonium halide containing one or more halogen atoms in the nucleus is known in literature and can be prepared by reaction of trimethylamine with p.methylbenzyl chloride halogenated in the nucleus, as is described in British patent No. 807,196, according to the scheme:

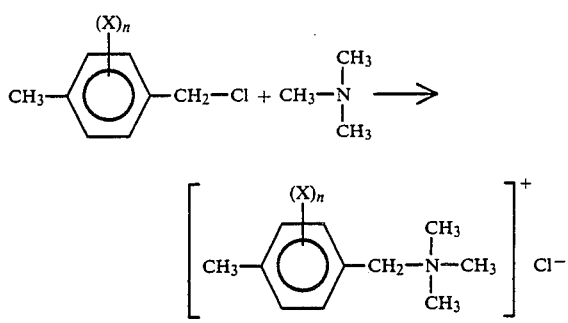

According to this invention, Hofmann elimination is conducted on halogen-substituted p.methylbenzyltrimethylammonium hydroxide of formula (III), at a temperature from 50° to 130° C. and for a time comprised between 0.5 and 20 hours, in the presence of an aqueous solution of an alkaline hydroxide, such as potassium hydroxide or sodium hydroxide, the concentration thereof being maintained below 40% by weight and preferably from 25 to 35%. Furthermore, it is preferred to maintain constant such concentration during the elimination step. Various measures can be taken to this purpose; generally it is preferable to remove the excess water by distillation.

Reaction times from 0.5 to 10 hours and temperatures ranging from 60° to 120° C. are preferred.

The Hofmann elimination can be also advantageously conducted in the presence of an inert organic solvent, such as e.g., toluene, xylene, benzene, dimethylsulfoxide and the like.

In the case of dihalogenation of (2,2)-paracyclophane, the process of the present invention permits to obtain, with industrially acceptable yields, i.e., higher than 25% by moles, a mixture of dihalogen-substituted isomers having a halogen on each ring and a degree of purity higher than 99%, and in particular free from mono- and/or tri-halogen derivatives.

In particular, through the process according to the present invention, when Hofmann elimination is accomplished from the chloro-derivative of p.methylbenzyltrimethylammonium hydroxide, it is possible to obtain an isomer mixture (mixture A) having the following composition:

30-50% by weight of 5,12-dichloro(2,2)-paracyclophane;
10-30% by weight of 5,11-dichloro(2,2)-paracyclophane;
20-40% by weight of 5,14-dichloro(2,2)-paracyclophane, and
5-15% by weight of 5,13-dichloro(2,2)-paracyclophane, wherein the sum of the isomers is equal to 100 and the content of dichloro-derivatives is higher than 99%.

It is expressly pointed out that 5,13-dichloro(2,2)-paracyclophane is not obtainable in appreciable amounts through the conventional processes for chlorinating (2,2)-paracyclophane.

From this mixture (A) it is possible to prepare, by means of a proper separation technique, for example, fractional crystallization, various mixtures (B) and (C) having a different isomeric composition, such as:

Mixture B 40-65% by weight of 5,12-dichloro(2,2)-paracyclophane,
30-55% by weight of 5,14-dichloro(2,2)-paracyclophane,
1-20% by weight of 5,13-dichloro(2,2)-paracyclophane, and
0-10% by weight of 5,11-dichloro(2,2)-paracyclophane; in which the sum of the isomers is equal to 100 and the content of dichloro-derivatives is higher than 99%.

Mixture C 65-99% by weight of 5,11-dichloro(2,2)-paracyclophane and
1-35% by weight of 5,13-dichloro(2,2)-paracyclophane.

Furthermore, since these mixtures, which are applied by means of the vapor vacuum deposition technique, have different chemical-physical characteristics, they are particularly suitable for specific fields of use. For example, isomeric mixture C permits to obtain films endowed with a high dielectric strength as is required in ferrite coating.

It is expressly pointed out, also, that said mixtures A, B and C are not obtainable through the processes of the art which comprise a direct halogenation on the preformed (2,2)-paracyclophane; thus, these mixtures are another object of this invention.

The present invention is further clarified by the following examples, which are to be construed as merely illustrative and not limitative of the invention.

In the following examples, all parts, percentages and ratios are by weight, unless otherwise indicated.

EXAMPLE 1

Into a 1 liter reactor, equipped with a stirrer, a thermometer and a condenser, there were charged, at room temperature:

50 g of chloro-p.methylbenzyltrimethylammonium chloride of formula:

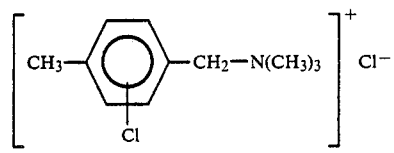

87 g of water,
43 g of NaOH and
500 ml of xylene.

The reaction mass was brought to 110° C. in about 3 hours and it was maintained at the boiling temperature for further 5 hours. In the course of boiling, water was distilled while maintaining the concentration of NaOH in the aqueous solution at about 33% by weight.

The reaction mass was filtered at 80° C. thus obtaining, after washing with xylene and water and drying, about 15.1 g of polychloro-p.xylene. The filtrate consisted of an alkaline aqueous phase and of a xylene solution, which were separated. The xylene solution was repeatedly washed with water up to full neutrality of the washing water, and subsequently it was subjected to distillation in order to remove the xylene.

13.1 g of an oily mixture were obtained. The mixture was made to flow through a liquid-liquid chromatography column, consisting of 200 g of SiO$_2$ and containing hexane as an eluent.

From the eluted hexane solution there were obtained, after removal of the solvent, 8.8 g (molar yield: about 30%) of a mixture (A) of isomers of dihalogenated (2,2)-paracyclophane of general formula:

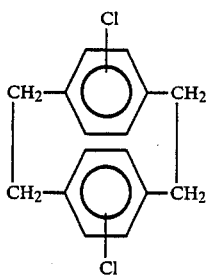

which, on gas-chromatographic analysis, revealed the following isomeric composition:

21% by weight of 5,11-dichloro-(2,2)-paracyclophane,

39% by weight of 5,12-dichloro-(2,2)-paracyclophane,

10% by weight of 5,13-dichloro-(2,2)-paracyclophane, and

30% by weight of 5,14-dichloro-(2,2)-paracyclophane.

The structure of the individual isomers was determined by NMR analysis. The purity degree, measured by gas-chromatography, was higher than 99%.

EXAMPLE 2

8.8 g of the isomer mixture obtained in Example 1 were hot-treated with 100 ml of hexane to boiling. After cooling, the mixture was filtered and the solid portion was dried, so obtaining 1.87 g of a mixture (C) which, on gas-chromatographic analysis, revealed the following isomeric composition:

85.7% by weight of 5,11-dichloro-(2,2)-paracyclophane, and 14.3% by weight of 5,13-dichloro-(2,2)-paracyclophane. The purity degree was higher than 99%.

From the filtrate there were obtained, by distillation of the solvent, 6.93 g of a mixture (B) which, on gas-chromatographic analysis, revealed the following isomeric composition:

3.6% by weight of 5,11-dichloro-(2,2)-paracyclophane, 49.5% by weight of 5,12-dichloro-(2,2)-paracyclophane, 8.8% by weight of 5,13-dichloro-(2,2)-paracyclophane, and 38.1% by weight of 5,14-dichloro-(2,2)-paracyclophane. The purity degree was higher than 99%.

EXAMPLE 3

Example 1 was repeated to obtain 13.1 g of an oily mixture. This mixture was treated with 100 ml of hexane to boiling temperature. After cooling, the solid portion was filtered, so obtaining a dichloro-(2,2)-paracyclophane mixture in an amount and with an isomeric distribution comparable with those of mixture (C) of Example 2.

The filtrate was eluted with hexane in a SiO$_2$ column following the same operating modalities of Example 1. Recovered was a mixture of dichloro-(2,2)-paracyclophanes in an amount and with an isomeric distribution comparable with those of mixture (B) of Example 2.

What is claimed is:

1. A process for preparing halogenated isomers of (2,2)-paracyclophane by Hofmann elimination, in an alkaline aqueous solution, from p.methylbenzyltrimethylammonium hydroxide halogen-substituted in the nucleus, of formula:

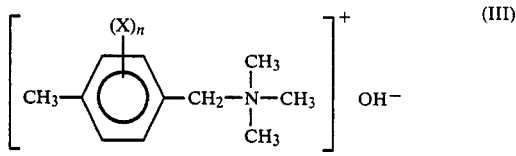

in which X is a halogen atom, and n is an integer from 1 to 4, in which the concentration of the alkaline hydroxide in the aqueous solution is maintained lower than 40% by weight during the Hofmann elimination reaction.

2. The process of claim 1, in which X in formula (III) is chlorine.

3. The process of claim 1, wherein the concentration of the alkaline hydroxide ranges from 25 to 35% by weight.

4. The process of claim 1, wherein the concentration of the alkaline hydroxide is maintained substantially constant during the course of the Hofmann elimination.

5. The process of claim 1, wherein p.methylbenzyltrimethylammonium hydroxide halogen-substituted in the nucleus and having general formula (III) is formed in situ by reaction of an alkaline hydroxide on the corresponding halide.

6. The process of claim 1, in which Hofmann elimination is conducted at a temperature from 50° to 130° C. and for a time of 0.5–20 hours.

7. The process of claim 6, in which Hofmann elimination is conducted for a time of 0.5 to 10 hours.

8. Mixtures of isomers of dihalogenated (2,2)-paracyclophanes having a halogen on each ring and a degree of purity higher than 99%, prepared according to the process of claim 1.

9. A mixture of isomers according to claim 8, having the following composition:

30–50% by weight of 5,12-dichloro-(2,2)-paracyclophane,

10–30% by weight of 5,11-dichloro-(2,2)-paracyclophane,

20–40% by weight of 5,14-dichloro-(2,2)-paracyclophane, and

5–15% by weight of 5,13-dichloro-(2,2)-paracyclophane, wherein the sum of the isomers is equal to 100% and the content of dichloro-derivatives is higher than 99%.

10. A mixture of isomers according to claim 8, having the following composition:

40–65% by weight of 5,12-dichloro-(2,2)-paracyclophane,

30–55% by weight of 5,14-dichloro-(2,2)-paracyclophane,

1–20% by weight of 5,13-dichloro-(2,2)-paracyclophane, and

0–10% by weight of 5,11-dichloro-(2,2)-paracyclophane, wherein the sum of the isomers is equal to 100% and the content of dichloro-derivatives is higher than 99%.

11. A mixture of isomers according to claim 8, having the following composition:

65-99% by weight of 5,11-dichloro-(2,2)-paracyclophane,
35-1% by weight of 5,13-dichloro-(2,2)-paracyclophane.

* * * * *